(12) United States Patent
Hopkins et al.

(10) Patent No.: US 7,488,942 B2
(45) Date of Patent: Feb. 10, 2009

(54) GAS SENSORS

(75) Inventors: Graham Paul Hopkins, Essex (GB); Andrew Stephen Hayward, Essex (GB)

(73) Assignee: E2V Technologies (UK) Limited, Chelmsford (GB)

( * ) Notice: Subject to any disclaimer, the term of this patent is extended or adjusted under 35 U.S.C. 154(b) by 251 days.

(21) Appl. No.: 10/534,281

(22) PCT Filed: Nov. 7, 2003

(86) PCT No.: PCT/GB03/04877

§ 371 (c)(1), (2), (4) Date: Apr. 10, 2006

(87) PCT Pub. No.: WO2004/042374

PCT Pub. Date: May 21, 2004

(65) Prior Publication Data

US 2006/0226367 A1    Oct. 12, 2006

(30) Foreign Application Priority Data

Nov. 7, 2002    (GB) ................... 0225995.0

(51) Int. Cl.
G01J 5/02    (2006.01)
(52) U.S. Cl. ..................................... 250/343
(58) Field of Classification Search ................ 250/343
See application file for complete search history.

(56) References Cited

U.S. PATENT DOCUMENTS

| | | |
|---|---|---|
| 3,749,495 A | 7/1973 | Wilkins et al. |
| 4,024,397 A | 5/1977 | Weiner |
| 4,557,603 A | 12/1985 | Oehler et al. |
| 4,668,635 A | 5/1987 | Forster |
| 5,009,493 A | 4/1991 | Koch et al. |
| 5,130,544 A | 7/1992 | Nilsson |
| 5,170,064 A | 12/1992 | Howe |
| 5,326,973 A | 7/1994 | Eckerbom et al. |
| 5,384,640 A | 1/1995 | Wong |
| 5,625,189 A | 4/1997 | McCaul et al. |

(Continued)

FOREIGN PATENT DOCUMENTS

DE    3326941    2/1985

(Continued)

OTHER PUBLICATIONS

Office Action issued in U.S. Appl. No. 10/516,334, filed Jun. 20, 2007.

(Continued)

*Primary Examiner*—David P Porta
*Assistant Examiner*—Mindy Vu
(74) *Attorney, Agent, or Firm*—Venable LLP; Robert Kinberg

(57) ABSTRACT

A gas sensor of the type having a housing defining a chamber within which light is transmitted from a source to a detector through an optical path, includes internal mirror portions having part ellipsoidal shape. Light is transmitted from a source to a detector via the reflective portions. The detector is arranged to sense light only from a limited range of angles, such that only light transmitted through a defined optical path reflected off the two reflective portions from the source reaches the sensor. This ensures that there is a constant optical path from the source to the detector, which improves the signal to noise ratio of the device.

14 Claims, 6 Drawing Sheets

U.S. PATENT DOCUMENTS

| | | | |
|---|---|---|---|
| 5,644,402 A | 7/1997 | Chevallet | |
| 5,973,326 A * | 10/1999 | Parry et al. | 250/343 |
| 5,977,546 A | 11/1999 | Carlson | |
| 6,016,203 A | 1/2000 | Martin | |
| 6,194,735 B1 | 2/2001 | Martin | |
| 6,313,464 B1 | 11/2001 | Schrader | |
| 6,469,303 B1 | 10/2002 | Sun et al. | |
| 2002/0063216 A1 | 5/2002 | Clausen et al. | |

FOREIGN PATENT DOCUMENTS

| | | |
|---|---|---|
| DE | 100 58 469 | 5/2002 |
| EP | 0 704 691 | 4/1996 |
| EP | 0 825 430 | 2/1998 |
| GB | 2 245 058 | 12/1991 |
| GB | 2 316 172 | 2/1998 |
| GB | 2 317 010 A | 3/1998 |
| JP | 5-215685 | 8/1993 |
| JP | 8-159971 | 6/1996 |
| JP | 9-184803 A | 7/1997 |
| JP | 9-229858 A | 9/1997 |
| SU | 1149146 | 4/1985 |

OTHER PUBLICATIONS

Office Action issued in U.S. Appl. No. 10/516,334, filed Apr. 2, 2008.

* cited by examiner

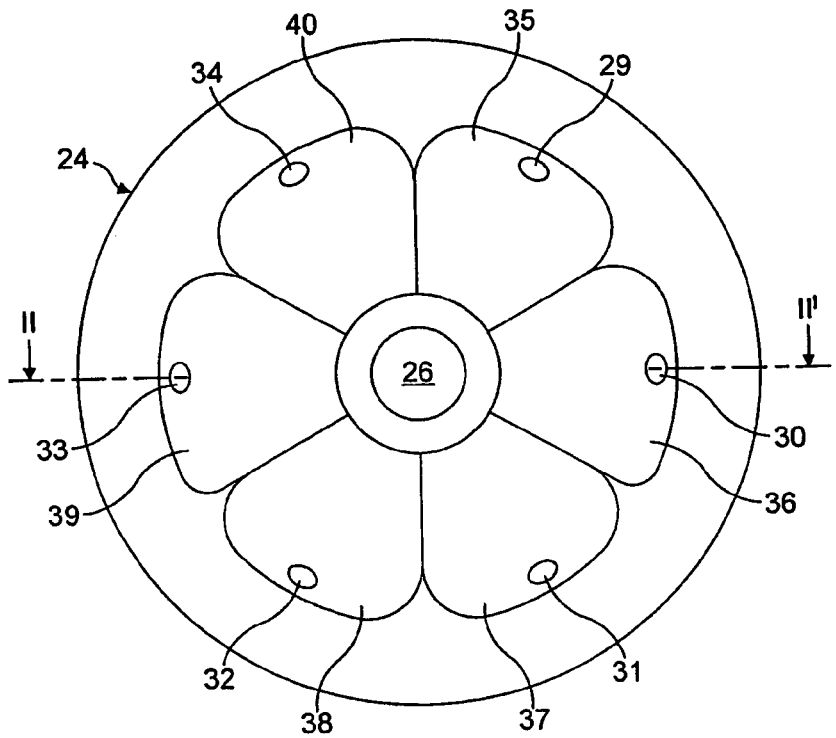
FIG. 4
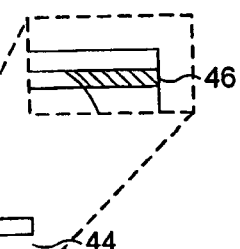
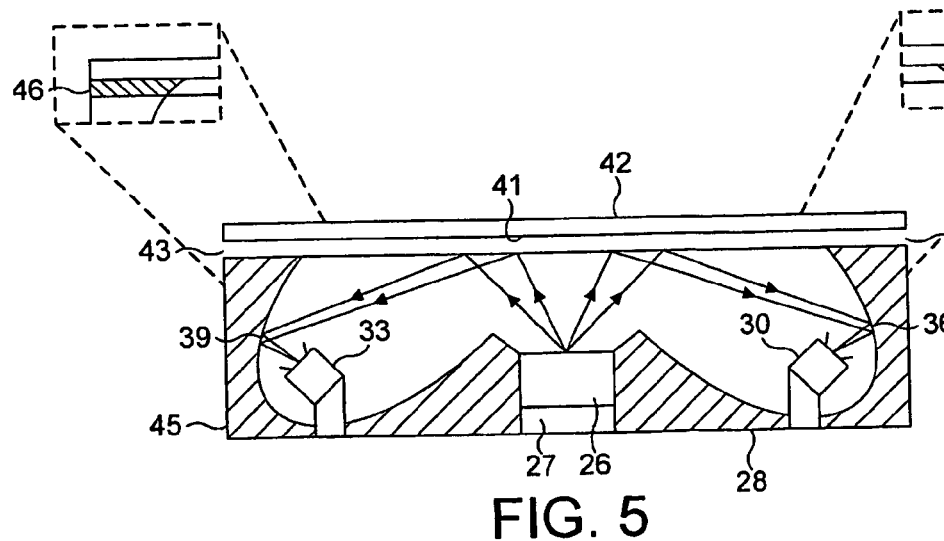
FIG. 6A  FIG. 6B
FIG. 5

GAS SENSORS

FIELD OF THE INVENTION

This invention relates to apparatus for, and methods of, sensing gasses. The invention particularly relates to such methods and devices in which optical radiation is transmitted through a gas and subsequently detected to provide information concerning the gas.

BACKGROUND OF THE INVENTION

In a typical gas sensor, an infrared source is arranged to emit radiation, which passes through a gas to be sensed. Infrared radiation is absorbed by the gas and that remaining is subsequently detected by an infrared detector, such as a photodiode, thermopile or pyroelectric detector. A comparison is made between the source intensity and the intensity of radiation detected following passage through the gas to give the concentration of a target gas. The concentration is related to the intensity by the following equation:

$$I = I \cdot e^{-\epsilon cl}$$

where I is the intensity of radiation detected by the detector, Io is the intensity of radiation emitted at the source, $\epsilon$ is effectively a constant which is dependent on the particular gas being monitored, c is the gas concentration and l is the distance travelled by the radiation through the gas.

We have appreciated problems with known detector arrangements. In particular, attempts have been made to fit multiple detectors into a single housing. Such an arrangement is shown in U.S. 2002/0063216, for example. However, such known systems suffer from inaccurate detection due to the physical limitations of the housing arrangement. We have appreciated the need, therefore, for an improved gas sensor containing multiple detectors within a housing.

SUMMARY OF THE INVENTION

Accordingly, there is provided a gas sensor comprising a chamber arranged to admit gas, a radiation source, and a plurality of detectors sensitive to radiation from the source, and a plurality of reflective curved surfaces, the detectors each being arranged to receive radiation from the source reflected by the respective curved surfaces of curvature such that light from the source is focused onto each detector.

The fact that respective reflective curved surfaces are provided allows radiation to be focused onto each detector improving the detection characteristics in a confined housing.

The reflective surfaces also reflect radiation from the source into desired optical paths. The reflective surfaces may have a plurality of foci. The source and the sensors may be located substantially at respective foci. Preferably, the source may be mounted in a central position, with the detectors arranged around the source.

The reflective surfaces may comprise a plurality of ellipsoids. The source and sensors may be located at a focus of respective ellipsoids. Alternatively, the ellipsoids may be arranged around the central region, with only the detectors being located at the foci of the ellipsoids. In any case, the ellipsoids advantageously have a common virtual focus. The ellipsoids provide a folded optical path for radiation from the source. This feature ensures that the detectors receive light of similar intensities. Further detail on ellipsoidal reflectors may be found in our British patent No. 2316172.

Of course, further sensors may be provided, and the inner surfaces of the chamber may be configured to provide more reflectors that are part ellipsoidal for the sensors.

The radiation source is preferably a light source, specifically an infrared source but sources and sensors operating in other parts of the optical radiation spectrum may be used in other embodiments.

BRIEF DESCRIPTION OF THE FIGURES

The invention will now be described, by way of example, with reference to the accompanying drawings, in which:

FIG. 4 is a plan view of a further alternative gas sensor constructed according to the invention;

FIG. 5 is a schematic sectional side view of the sensor of FIG. 4 along the line II-II;

FIGS. 6a and 6b illustrate alternative embodiments of the gas admittance regions of the sensor of FIG. 5;

DESCRIPTION OF PREFERRED EMBODIMENTS

Two embodiments of the invention will be described both of which use curved surface portions within a gas sensor housing to concentrate radiation (preferably IR light) from at least one source to a plurality of detectors. In the first embodiment, a single omnidirectional source is focused onto a plurality of detectors via a planar surface and respective curved surfaces associated with each detector. This embodiment has the advantage that an inexpensive omnidirectional source may be used. In the second embodiment, a separate source is provided for each sensor and is preferably a directional source so that light is concentrated from source to detector via the curved surface. In either embodiment, a plurality of detectors can fit into an industry standard housing size without deterioration of detection quality.

Figure 1:
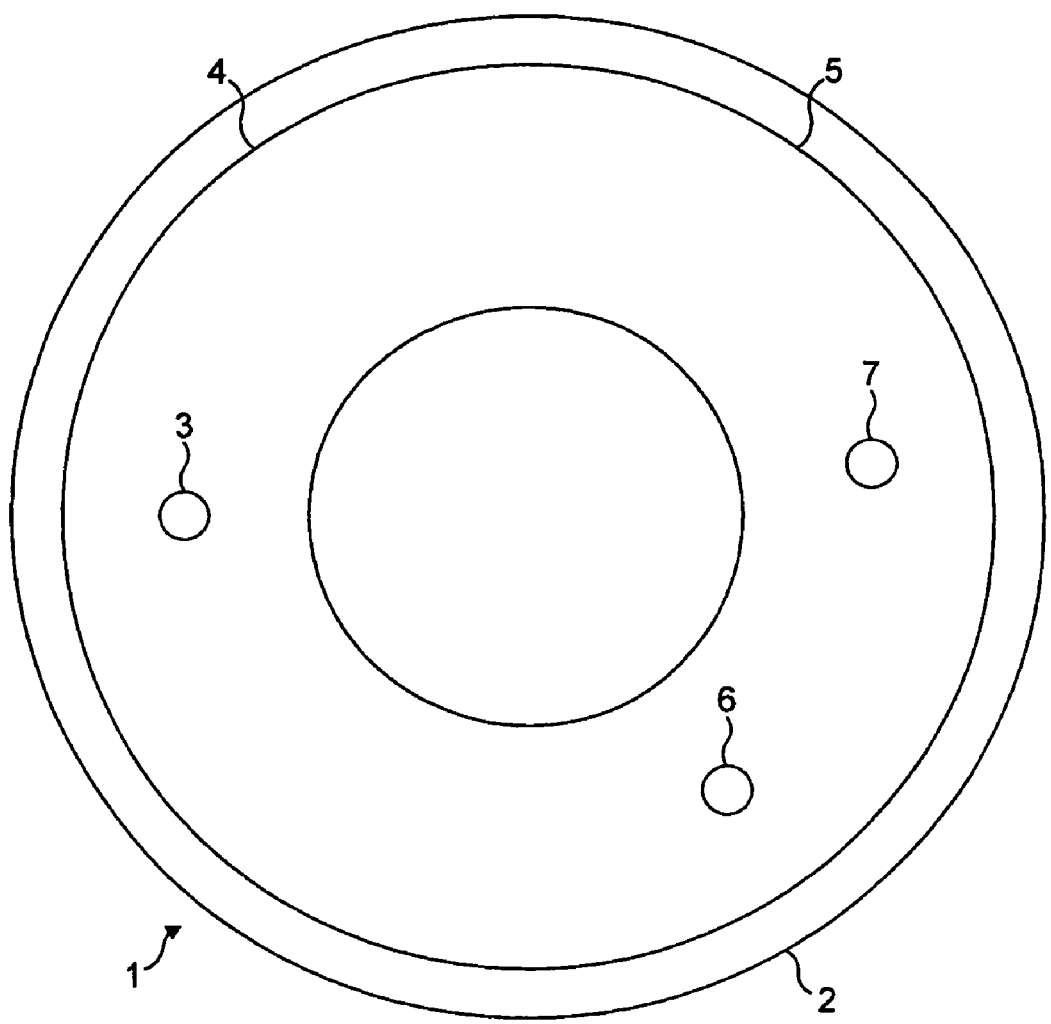
FIG. 1 is a plan view of a gas detector.

With reference to FIG. 1, a gas sensor is shown and indicated generally by the reference numeral 1. The detector 1 comprises a housing 2, which is preferably flameproof, and which contains a source 3 of infrared radiation. Interior surfaces of the housing 2 are reflectors of infrared radiation.

The interior of the housing 2 includes two partially overlapping part ellipsoids 4,5. The source 3 is placed substantially at the focus of the first part ellipsoid 4. A first detector 6 is located in the chamber in a predetermined position such that a portion of light from the source 3 reaches the detector 6 via predetermined optical paths. This first sensor may be arranged to detect gasses having high IR absorption coefficients, as the optical path length between this sensor and the source 3 is relatively short.

A second detector 7 is located at the focus of the second part ellipsoid 5. As seen in plan view, the second detector 7 is located opposite the source 3. The optical path length between the source 3 and this detector 7 is relatively long, compared with the optical path length between the source 3 and the first detector 6. Hence, this detector 7 may be suitable for detecting gasses having low IR absorption characteristics. The configuration of the interior reflective surfaces of the housing 2 and locations of the source 3 and detectors 6, 7 are such that infrared radiation emitted from the source 3 travels predetermined optical paths to the detectors 6,7, via the part ellipsoidal surfaces 4, 5.

A constraint for gas sensors of the type described is the need to be small, typically an industry standard size of housing 2 of diameter 20 mm and depth 19 mm, whilst retaining as long an optical path length from source to detector as possible. Another industry standard size to which the invention could equally apply is 32 mm diameter. The long optical path length is needed to ensure best sensitivity for gases of low concentrations. The longer the path length, the greater the effect on attenuation of light at the absorption band of the gas and hence the better the signal to noise ratio. However, we have also appreciated that the path length should be substantially constant for all light transmitted from the source to the detector. If light is able to travel through differing path lengths from source to detector, then any change in intensity on introduction of the gas to be analysed will differ depending upon the path length. As a result, the variation due to the gas to be analysed in comparison to variation due to other factors, such as other gasses or errors due to temperature changes, will be reduced. This effectively worsens the signal to noise ratio. The embodiments are preferably one of the industry standard sizes.

Figure 2:
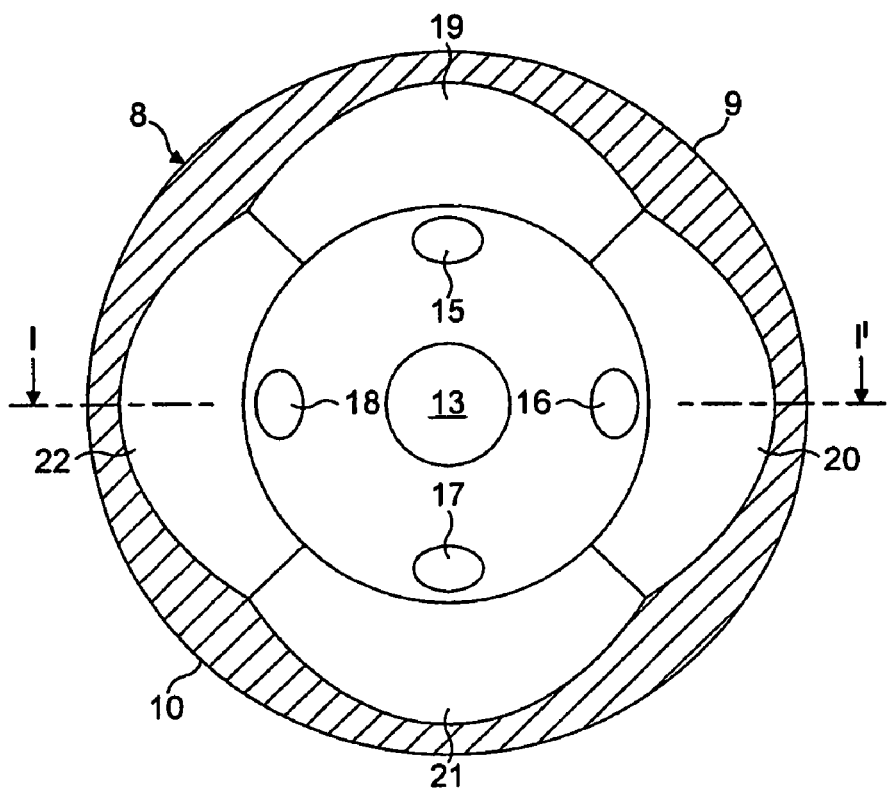
FIG. 2 is a plan view of a gas sensor constructed according to the invention.
Figure 3:
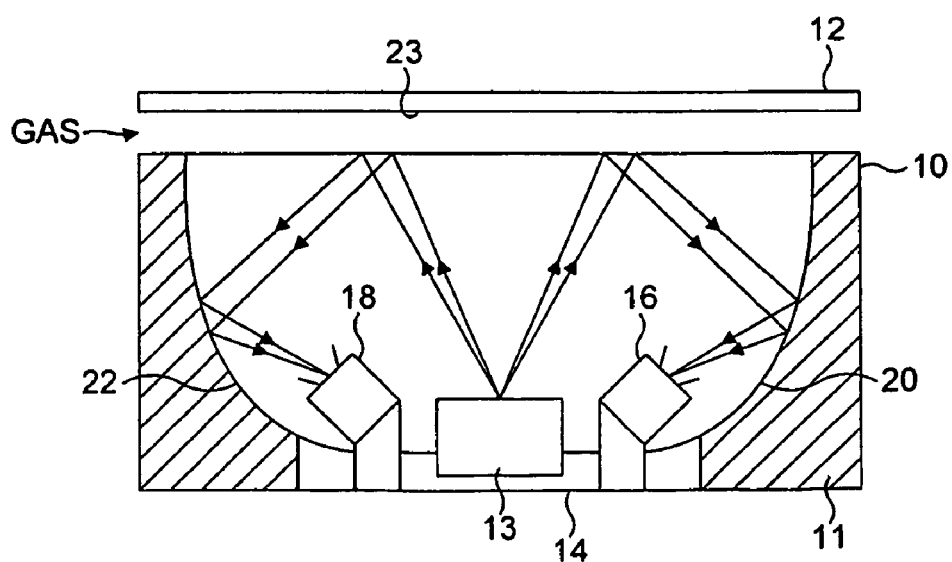
FIG. 3 is a schematic sectional side view of the sensor of FIG. 2 along the line I-I.

A first embodiment of the invention is illustrated in FIGS. 2 and 3. With reference to FIGS. 2 and 3, a gas sensor is shown and indicated generally by the reference numeral 8. The sensor 8 comprises a housing 9, which is preferably flameproof. The housing 9 comprises a generally cylindrical wall 10 with end walls 11 and 12. The housing 9 contains a source 13 of infrared radiation that, in this embodiment, is located approximately in a central region 14 of the end wall 11. The source is arranged to emit infrared radiation over a wide range of angles.

In accordance with the invention, the sensor 8 includes a plurality of infrared detectors 15, 16, 17 and 18. The detectors 15 to 18 inclusive are also mounted in the end wall 11 and are located at the foci of respective part-ellipsoids defined by curved walls 19, 20, 21 and 22 respectively. The curved walls 19 to 22 are arranged around the central region 14, so that the four ellipsoids are equally spaced around the inner circumference of the cylindrical housing 9. Thus, the arrangement of detectors 15 to 18 around the source 13 is substantially symmetrical as seen in the plan view of FIG. 2, the detectors being equidistant from the source.

With reference to FIG. 3, the reflective walls 20 and 22 associated with detectors 16 and 18 are shown. Each wall is curved in three dimensions to define a part ellipsoid. Detector 16 is located at a focus of the part ellipsoid defined by wall 20. Similarly, detector 18 is located at a focus of the part ellipsoid defined by wall 22. The end wall 12, opposite that on which the source 13 and detectors 15 to 18 are mounted, has a reflective inner surface 23, which is planar.

The configuration of the reflective surfaces 19 to 23 and locations of the source 13 and detectors 15 to 18 are such that infrared radiation emitted from the source 13 is directed onto the planar surface 23, from which it is reflected and directed onto the part-ellipsoidal surfaces. Radiation is reflected by the reflective surfaces 19 to 22 to the respective detectors 15 to 18, where the radiation is focused. Thus, the radiation undergoes two reflections before being received at the detectors. In this embodiment, the optical path lengths of radiation travelling from the source 13 to the detectors 15 to 18 are substantially equal.

The ellipsoids defined by the surfaces having detectors at the focus are arranged to have a substantially common virtual focus.

The detectors 15 to 18 are directional, i.e. arranged to detect radiation incoming from a predetermined directional range. Preferably, the directional range comprises a predetermined solid angle.

Figure 3A:
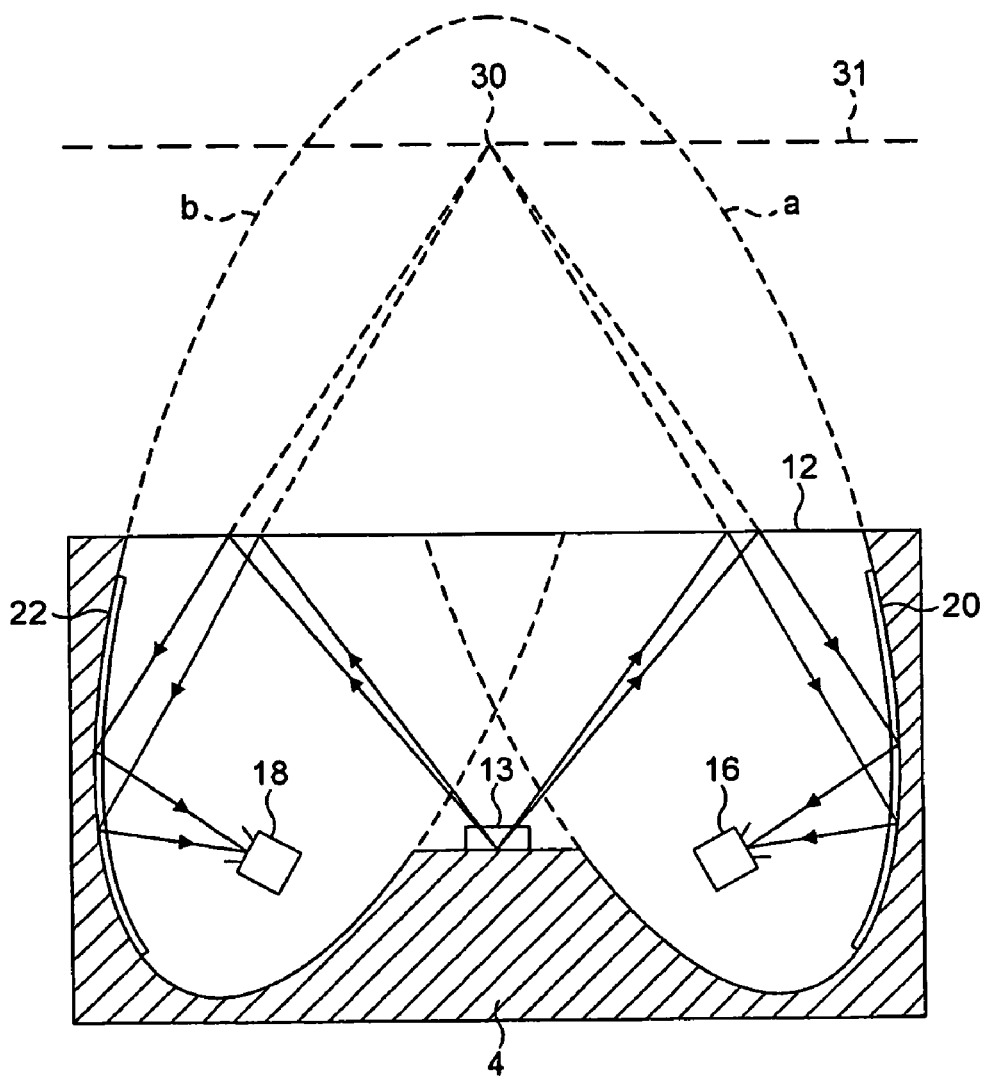
FIG. 3A is a further view of the sensor of FIG. 2 giving the geometry of the surfaces.

In conjunction with the ellipsoidal surface portions, this ensures that light from the source to the detector within the limited range of angles all travels the same path length. This fact can be proven according to the geometry, but can be seen empirically with reference to FIG. 3A which illustrates the general principles of FIG. 3 and the differences in presentation are immaterial to the principle demonstrated. Light from the source 13 is reflected from surface portions 20, 22 being shaped as portions of ellipsoids "a" and "b". This light is focused as if from a point 80, but reflected back from a planar reflective portion of the inner surface of the wall 12. The source 13 is effectively at an image of the detectors 16, 18. This "folded" arrangement reduces the height of the sensor by roughly half whilst maintaining the path length. The arrangement shown allows multiple detectors to sense light from a single central source. The path length of rays from the source to detector does not vary with the angle to the detector because it is a property of an ellipse that the path length of a ray from one focus to another reflected via the surface is the same irrespective of angle. Thus, by the detectors each limiting the solid angle of rays that reach the detector, only rays reflected via the respective ellipsoidal surface are detected and hence the path length of all such rays is the same.

Figure 3B:
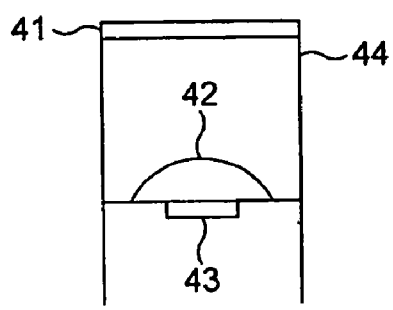
FIG. 3B shows directional sensors in more detail.

An example detector is shown in FIG. 3B. The detector comprises the active detector portion 43, here mounted to an immersion lens 42 behind an optical filter 41 within a housing 44. The immersion lens 42 defines the range of angles of acceptance focused to the active device 43. As previously described, the prime benefit is in avoiding stray light paths, but this also ensures that the light passing through filter 41 that is sensed travels at a near normal angle. The filter is of a wave plate type, and so near normal incidence ensures best bandpass performance.

This arrangement also ensures that the detector collects radiation from a narrow cone of light, the solid angle being typically 10-12°. The meaning of "narrow" in this context is sufficiently limited that primarily rays reflected from the respective reflective surface only reach the detector. The angles 10-12° are one such example.

A variation of the first embodiment is shown in FIGS. 4 and 5. This variation operates on the same principles as that shown in FIGS. 2 and 3, but has 6 detectors rather than 4. In this embodiment, a gas sensor 24 comprises a housing 25, in which is located a source 26 of infrared radiation. The source 26 is mounted in a central region 27 of a wall 28 of the sensor 24. Six detectors 29 to 34 are mounted in the wall 28. Each detector is equidistant from the source and the detectors are uniformly spaced around the interior of the cylindrical housing 25. Each detector 29 to 34 is associated with a part-ellipsoidal surface (35 to 40 respectively), and each detector is located at the focus of the ellipsoid defined by the surface.

Radiation emitted by the source 26 is reflected by a planar surface 41 associated with the upper wall 42 of the sensor. Radiation reflected by the surface 41 is directed towards the part-ellipsoidal surfaces 35 to 40, each of which directs radiation onto its respective detector. Radiation is directed from the source to each detector via distinct predetermined optical paths.

The provision of a plurality of detectors permits a plurality of gasses to be detected. The detectors may incorporate bandpass filters having different or overlapping frequency bands in order to facilitate the detection of target gasses.

It is preferable to be able to allow gas to pass in and out of the housing as quickly as possible, to increase the likelihood of a positive and rapid identification of the target gas, and a measure of its concentration. In the embodiment shown in FIGS. 4 and 5, an inlet port 43 and an outlet port 44 are provided, through which gas may be directed to pass into the housing 25. The ports 43, 44 are embedded in diametrically opposite sides of the cylindrical wall 45.

FIGS. 6a and 6b illustrate alternative gas admittance means. In this arrangement, regions 46 of the cylindrical wall 45 not providing reflective surfaces for the light may include particulate filters, mesh or sintered material.

Figure 9:
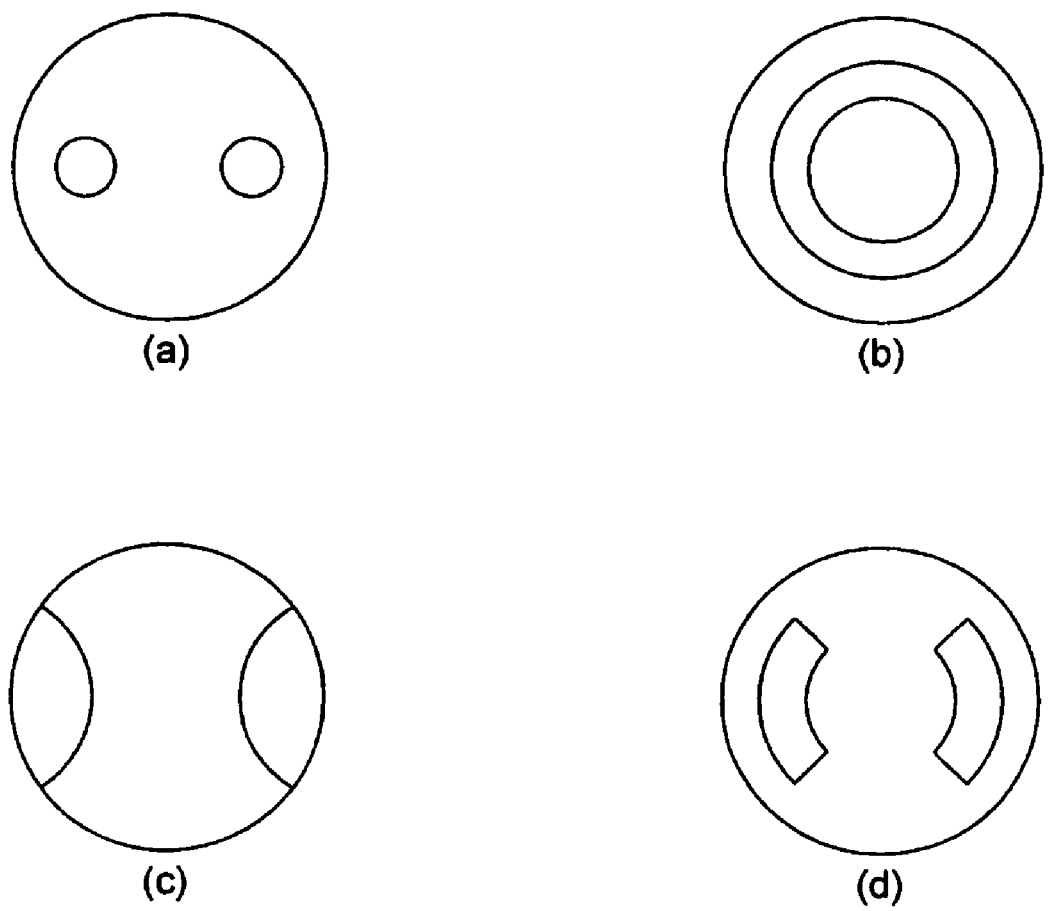
FIG. 9 shows arrangements of reflective surface.

In any of the sensors shown in FIGS. 2 to 5, the gas admittance may be part of the upper wall 12, 42 not bearing a reflective surface. This can be achieved because only a selected portion or portions of the upper wall need to be reflective. This is because the possible range of angles of rays is limited and so only contains portions or "patches" of the upper surface perform a reflection function (this is described later in relation to FIG. 9). As a result, gas admittance can be through part of the upper surface having, for example, a sintered mesh.

Figure 7:
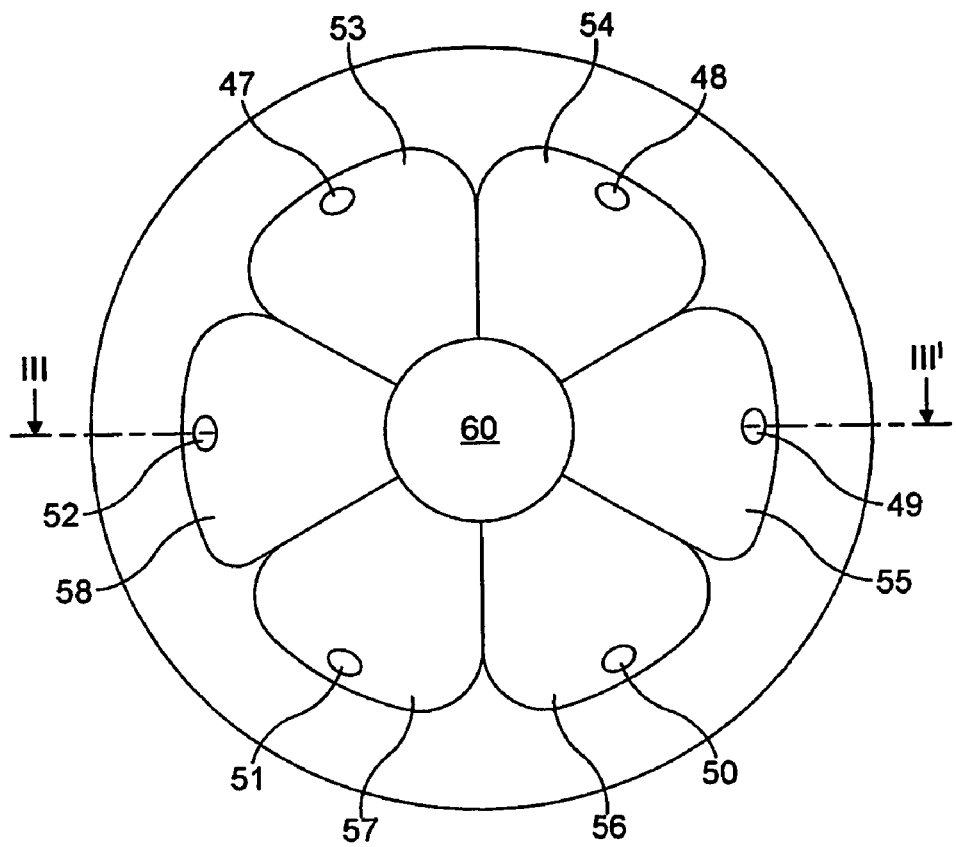
FIG. 7 is a plan view of a further alternative gas sensor constructed according to the invention.
Figure 8:
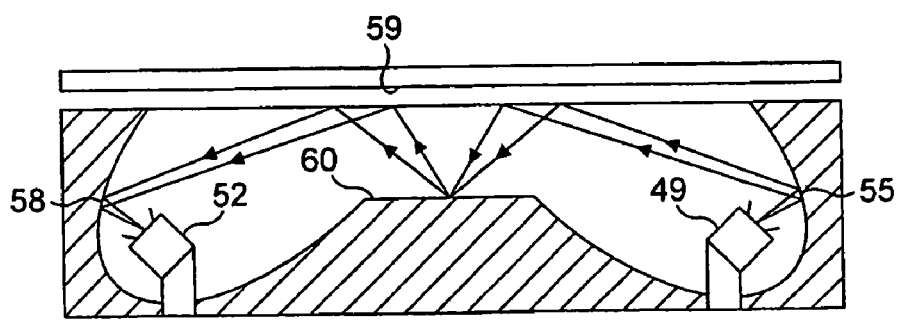
FIG. 8 is a schematic sectional side view of the sensor of FIG. 2 along the line III-III.

In the above embodiment, a solitary source is employed. However, in the embodiment of FIGS. 7 and 8, a plurality of sources 47, 48, 49 are incorporated in the gas sensor. Each source 47, 48, 49 is associated with a detector 50, 51, 52 respectively. Each detector 50, 51, 52 is mounted diametrically opposite its source. Each of the sources and detectors are located at the foci of respective part-ellipsoidal reflective surfaces 53 to 58. Light emitted by each source is reflected by the associated part-ellipsoidal surface, and is also reflected by the planar surface 59 associated with the upper wall of the housing and a central reflective surface 60.

The housing may include a reference detector for compensating for changes in operating conditions and with time. The reference detector includes a different filter to those fitted in the active detectors and does not respond to the target gas. By comparing the signals from at least one of the active detectors and the reference detector, the user can discriminate the signal reduction due to the target gas from that due to ambient and physical variations. The reference detector is preferably located immediately adjacent an active detector so that the detector and reference collect radiation that has travelled similar optical paths. To aid this, the reference detector may be contained in a single detector package with an active detector.

A suitable infrared source is a wide-angle tungsten lamp, which provides a broadband infrared thermal source. Other sources include LEDs, lasers or diodes with lenses, especially immersion lenses. A diffuser may be placed over the infrared source in order to reduce filament imaging effects. This also improves the thermal stability of the gas sensor and also renders the device less sensitive to movements of the filament.

A particular feature of the embodiments is that using a combination of the directional detector and part ellipsoidal surfaces allows multiple sensors to be used with a single source as shown in FIGS. 2 and 3. This allows a simple tungsten lamp to be used as the source (or other omnidirection IR source) yet the path length of rays to the detectors is the same for all rays within the angle of acceptance of the detector. This allows multiple sensors to be used within a single housing without stray light causing a loss of detection quality.

In order to reduce the amount of stray light within the gas sensor, reflective barriers or collimators may be provided around the source of infrared radiation and/or the detectors.

A diffuser may also be placed over one or more of the detectors in order to reduce reflective cusps or imaging effects. This further improves the thermal stability of the gas sensor and gives greater immunity to localised changes in reflectance.

The reflective surfaces may comprise layers of plated gold to provide good reflectance. At least some of the reflective areas may comprise coatings of a matt gold finish. The provision of matt gold further reduces reflective cusps or imaging effects, as well as further improving the thermal stability of the gas sensor and giving greater immunity to localised changes in reflectance.

The matt gold reflectors ensure that the detectors are much less prone to manufacturing tolerances and the effects of changes caused by heat. The matt surface slightly de-focuses the radiation so that a diffused spot is focused on the detector rather than a tightly focused spot created by highly polished surfaces. If this diffused spot moves around the detector surface there is little change in the response.

FIG. 9(a)-(d) shows possible arrangements for reflective surface portions of the upper surface.

The length of the optical path through the chamber may be altered by adjusting the relative positions of the sensors and source. Further alterations in optical path length may be achievable by adjusting the separation between the planar reflective surfaces. Alternatively, or additionally, the dimensions of the inner surfaces of the chamber may be changed so that the ellipsoids they represent are of different sizes or have a different angular separation.

The optical paths between sensor and source may have the same or different lengths. Gasses having high IR absorption characteristics need only a short optical path to provide suitable concentration resolution. Gasses having low IR absorption characteristics require a relatively long optical path.

Alternatively, the invention enables a target gas to be detected with greater certainty. If the gas is present in high concentrations, then only a short optical path is needed for detection. If the target gas is present in low concentrations, then a longer optical path is required in order to firmly identify the concentration of the gas in the sample. This can be arranged by choosing the distance between source and detector by varying the dimensions of the reflective surfaces.

The chamber may be a single component or may comprise a plurality of pieces. A suitable manufacturing process for the contours of the chamber is that of machine turning. Alternatively, moulding in plastics or metal injection may be utilised. These processes are well known industrial techniques and may be readily employed by the skilled person.

The invention claimed is:

1. A gas sensor comprising a chamber arranged to admit gas, a radiation source, a plurality of detectors sensitive to radiation from the radiation source, and a plurality of respective reflective curved surfaces, the detectors being circumferentially arranged around the radiation source and each detector being arranged to receive radiation from the radiation source reflected by the respective curved surfaces of curvature such that radiation from the radiation source is focussed onto each detector, the radiation source and plurality of detectors being arranged within the chamber.

2. A gas sensor as claimed in claim 1, wherein the source is located substantially at a first focus of each respective reflective curved surface.

3. A gas sensor as claimed in claim 1, wherein each detector is located substantially at a second focus of each respective reflective curved surface.

4. A gas sensor as claimed in claim 1, wherein the reflective curved surfaces are part ellipsoidal surfaces.

5. A gas sensor as claimed in claim 4, wherein one of the detectors is at a focus of a first part ellipsoidal surface, a second detector is at a focus of a second part ellipsoidal surface and the first and second ellipsoids share a common virtual focus.

6. A gas sensor as claimed in claim 5, wherein the first detector is arranged to detect a first predetermined gas and the second detector is arranged to detect a second predetermined gas.

7. A gas sensor as claimed in claim 1, further comprising a central region between the detectors, there being one source located in the central region.

8. A gas sensor as claimed in claim 7, further comprising a further reflective surface so arranged that radiation from the one radiation source is reflected by the further reflective surface onto each respective reflective curved surface and then to each respective detector.

9. A gas sensor as claimed in claim 8, wherein the further reflective surface comprises an annular reflective surface.

10. A gas sensor as claimed in claim 7, wherein the one source is generally omnidirectional.

11. A gas sensor as claimed in claim 1, further comprising a reference detector.

12. A gas sensor as claimed in claim 1, wherein the radiation source is an infrared source.

13. A gas sensor as claimed in claim 1, wherein the source is arranged to heat substantially all the surfaces from which radiation is reflected to a temperature above ambient temperature.

14. A gas sensor as claimed in claim 1, wherein each detector is arranged to receive radiation from a narrow solid angle.

* * * * *